United States Patent [19]

Goodson et al.

[11] Patent Number: 4,735,603
[45] Date of Patent: Apr. 5, 1988

[54] LASER SMOKE EVACUATION SYSTEM AND METHOD

[75] Inventors: James H. Goodson, 3600 Gaston Ave., Dallas, Tex. 75246; Millard M. Judy; Rex A. Moses, both of Dallas, Tex.

[73] Assignee: James H. Goodson, Dallas, Tex.

[21] Appl. No.: 905,823

[22] Filed: Sep. 10, 1986

[51] Int. Cl.[4] .............................................. A61N 1/30
[52] U.S. Cl. ........................................ 604/21; 604/26; 604/28; 604/35; 604/118; 604/317; 128/303.1; 128/747
[58] Field of Search .................................... 604/19–24, 604/26–28, 29, 31, 35, 118–120, 317–319, 320, 43–45; 128/303.1, 747.1 R, 395–398, 6, 202.12; 15/346

[56] References Cited

U.S. PATENT DOCUMENTS

| | | | |
|---|---|---|---|
| 3,505,989 | 4/1970 | Truhan | 128/1 R |
| 3,982,541 | 9/1976 | L'Esperance, Jr. | 604/20 |
| 4,211,229 | 7/1980 | Wurster | 128/395 |
| 4,381,007 | 4/1983 | Doss | 128/303.1 |
| 4,487,606 | 12/1984 | Leviton et al. | 604/319 |
| 4,638,800 | 1/1987 | Michel | 128/303.1 |

OTHER PUBLICATIONS

Steptoe, "Laparoscopy in Gynaecology", pp. 12–29, 1967.
Lotze, "Safety Considerations and Clinical Points Relating to Proper Application of Laser Surgery"; Woman's Hospital of Texas; 7/85.

Primary Examiner—C. Fred Rosenbaum
Assistant Examiner—Mario Costantino
Attorney, Agent, or Firm—H. Mathews Garland

[57] ABSTRACT

A laser smoke evacuation system and method for laser smoke removal from the site of laser laparoscopy in a patient cavity. The system includes a $CO_2$ gas pump connected through a control valve, a pressure sensor, and a bacterial filter to a laparoscopic tube inserted into the patient, a return line from a second laparoscopic tube in the patient through a smoke filter, a pressure sensor, a control valve, and a fluid trap into the return of the pump, and an insufflator connected into the patient to supply $CO_2$ gas lost by leakage and tissue absorption an to provide required distention of the patient cavity. The method includes the steps of supplying a first flow of $CO_2$ gas into a patient cavity to the operation sites, returning the first flow of $CO_2$ gas with removed laser smoke from the cavity, cleansing the smoke from the first flow of $CO_2$ gas, recirculating the cleansed first flow of $CO_2$ gas back to the patient, and providing a second makeup flow of $CO_2$ gas to the patient to replace $CO_2$ gas from the first flow lost by leakage and tissue absorption and provide cavity distention.

20 Claims, 3 Drawing Sheets

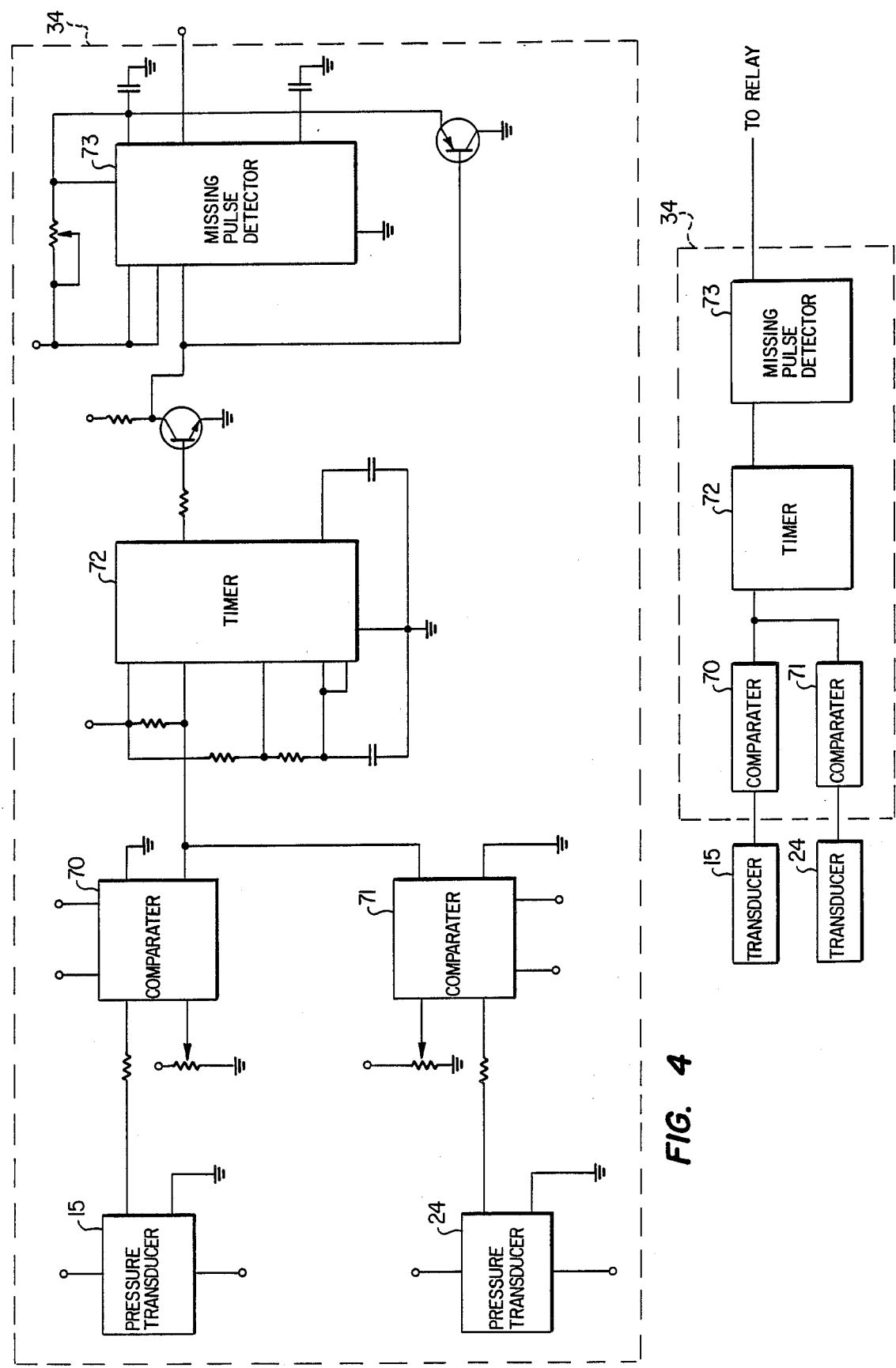

LASER SMOKE EVACUATION SYSTEM AND METHOD

FIELD OF THE INVENTION

This invention relates to surgical procedures and more specifically relates to a system and method for providing a smoke-free environment at an operation site in a patient cavity during laser laparoscopy.

HISTORY OF THE PRIOR ART

Laser laparoscopy is a surgical procedure in which a focused laser beam, typically from a $CO_2$ laser, is transmitted in a laparoscopic tube through the abdominal muscular wall of a patient into the pelvis where the laser beam is used to excise or remove body tissue by vaporization. This laser surgical procedure is used to treat a number of gynecological problems including hydrosalpinx, endometriosis, endometrioma, small uterine fibroids, and pelvic adhesions. The only surgical opening required is a small incision through the abdominal wall because the laparoscopic tube is small, typically about 12.7 mm in diameter. Use of this procedure avoids the risk of laparotomy requiring full size abdominal incisions. The major problem encountered, however, during laser laparoscopy is the removal of vapor or smoke produced by the ablation of the body tissue. One technique which has been used for intermittent smoke removal has employed suction tubes with valves. A problem with such a smoke removal procedure is the loss $CO_2$ gas which is required to sustain abdominal distention. The required abdominal distention for the laser procedure necessitates replacing the lost $CO_2$ gas. No system is presently available which will effect sustained smoke removal preventing its build up in vicinity of the tissue removal whether laser laparoscopy is carried out by either the two or three puncture techniques. The vapor consist of water vapor and carbonaceous vapors from the decomposition of organic material of the tissue. A small manually operated valve is presently used with operating room wall suction. This permits a small volume of intermittant smoke and $CO_2$ gas withdrawal as it is generated by the lasing. This withdrawal must be followed by an input of replacement $CO_2$ gas from an insufflator. Use of large replacement volumes of $CO_2$ gas characteristic of repeated abdominal evacuations can lead to problems in maintaining the blood physiological acid base balance due to the formation of the $HCO_3^-$ ion from absorbed $CO_2$ gas.

SUMMARY OF THE INVENTION

It is a principal object of the invention to provde a new and improved surgical procedure.

It is another principal object of the invention to provide a new and improved surgical procedure for use during laser laparoscopy.

It is another object of the invention to provide apparatus and techniques for the removal of smoke produced within a patient during a laser laparoscopy.

It is another object of the invention to provide apparatus and techniques for the removal of smoke during laser laparoscopy wherein abdominal distention is sustained during the procedure.

It is another object of the invention to provide apparatus and methods for smoke removal during laser laparoscopy wherein real-time smoke removal is effected and its buildup is prevented while simultaneously retaining constant abdominal volume and steady state insufflation pressure without introducing large replacement volumes of $CO_2$.

It is another object of the invention to provide methods and apparatus of the character described wherein closed circuit circulation is maintained and $CO_2$ gas is not lost during the smoke removal.

It is another object of the invention to provide methods and apparatus of the character described wherein physiological blood $CO_2$ gas balance is maintained in equilibrium.

It is a still further object of the invention to provide a laser laparoscopy surgical procedure for smoke removal which interfaces with standard laser laparoscopic system.

In accordance with the invention there is provided a closed circuit system for smoke and vapor removal during laser laparoscopy which includes a $CO_2$ gas pump, a discharge line connected with the pump through a control valve, a pressure sensor, a bacteria removal filter, into the patient and a discharge line from the patient through a smoke removal filter, a pressure sensor, a control valve, a fluid trap, back into the return line to the pump. An insufflator is connected through a discharge line into the cavity of the patient for maintaining the required pressure in the cavity and replacing $CO_2$ gas lost through leakage.

In accordance with the method of the invention smoke removal is effected from the cavity of a patient during laser laparoscopy including the steps of: pumping $CO_2$ gas through a control valve, and a bacteria removal filter into a cavity of a patient at the site of laser laparoscopy while controlling the pressure of the input gas; return flowing the $CO_2$ gas with smoke generated at the site of the laparoscopy procedure from the cavity of the patient; removing the smoke by filter means from the discharge flow from the patient; returning the filtered discharge flow of $CO_2$ gas through a control valve and trap to pump means for recirculation to the patient; maintaining the required distention of the cavity by flow of $CO_2$ gas from a source separate from the recirculation system; and providing make up $CO_2$ gas to replace leakage and tissue absorption from the separate $CO_2$ gas source.

BRIEF DESCRIPTION OF THE DRAWINGS

The forgoing objects and advantages and preferred embodiments of the apparatus and method of the invention will be better understood from the following detailed description thereof taken in conjunction with the accompanying drawings wherein:

FIG. 3 is a functional schematic of the control module including the comparison and time delay functions;

FIG. 4 is a detailed diagram of the control module as shown in FIG. 3;

DETAILED DESCPRIPTION OF THE PREFERRED EMBODIMENT

Figure 1:
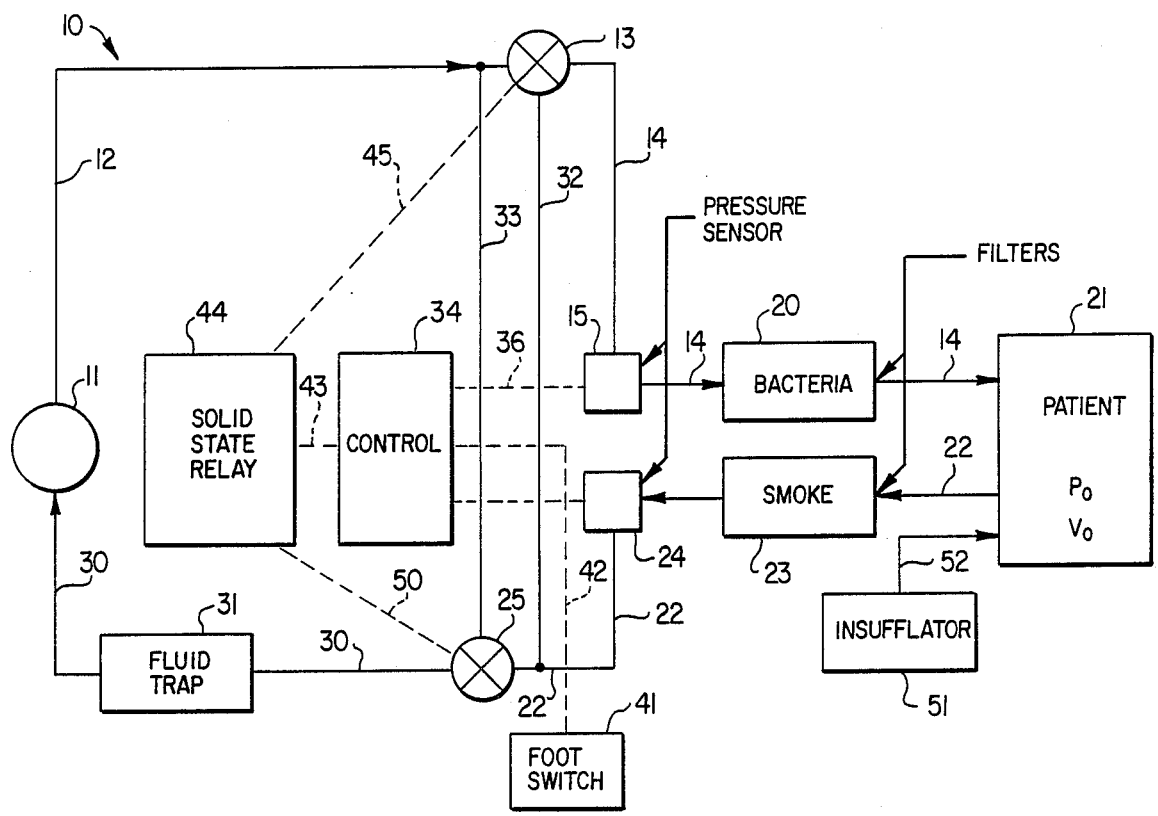
FIG. 1 is a schematic flow diagram of the system of the invention.

Referring to FIG. 1, the closed circuit $CO_2$ gas circulation system 10 embodying the features of the invention includes a $CO_2$ pump 11 connected with a discharge line 12 extending to a solenoid flow control valve 13. A $CO_2$ discharge line 14 is connected from the valve 13 through a pressure transducer 15 and a bacteria filter 20 into a patient 21 upon whom the surgical procedure is being performed. A recirculating or return line 22 is connected from the patient through a smoke removal filter 23 and a pressure transducer 24 into a solenoid flow control valve 25. A recirculating line 30 connects through a fluid trap 31 into the suction side of the $CO_2$ pump 11. A bypass or shunt on line 32 is connected from the valve 13 into the recirculating line 22. Another shunt or bypass line 33 is connected from the valve 25 to the supply or pump discharge line 12. A control module 34 is connected by electrical lines 35 and 40 to two pressure transducers 15 and 24, respectively. A foot operated switch 41 is connected by an electrical line 42 with the control module. The control module is also connected by a electrical line 43 with a relay 44 which is connected with and operates the valves 13 and 25 by electric lines 45 and 50, respectively. An insufflator 51 is connected through a flow line 52 into the patient cavity to maintain the distention of the cavity while the operation is being carried out and to supply make up $CO_2$ gas lost through leakage and tissue absorption. The flow lines 14, 22, and 52 may connect the recirculating system and the insufflator into the patient maybe as shown in either FIG. 5 or FIG. 6. In the two puncture technique of FIG. 5, the input line 14 of the recirculating system and the flow line 52 from the insufflator are connected into the patient through a single laparoscope tube 53 which also directs the laser beam to the operation site and has means for viewing by the surgeon. The laparoscope tube 53 is a standard available laser surgical instrument. In the two puncture technique, the return or recirculating of the $CO_2$ gas and the smoke generated by the laser operation passes through a second laparoscope tube 54 which is connected to the recirculating line 22. The laparoscope 54 also is a standard available laser surgical instrument.

Figure 6:
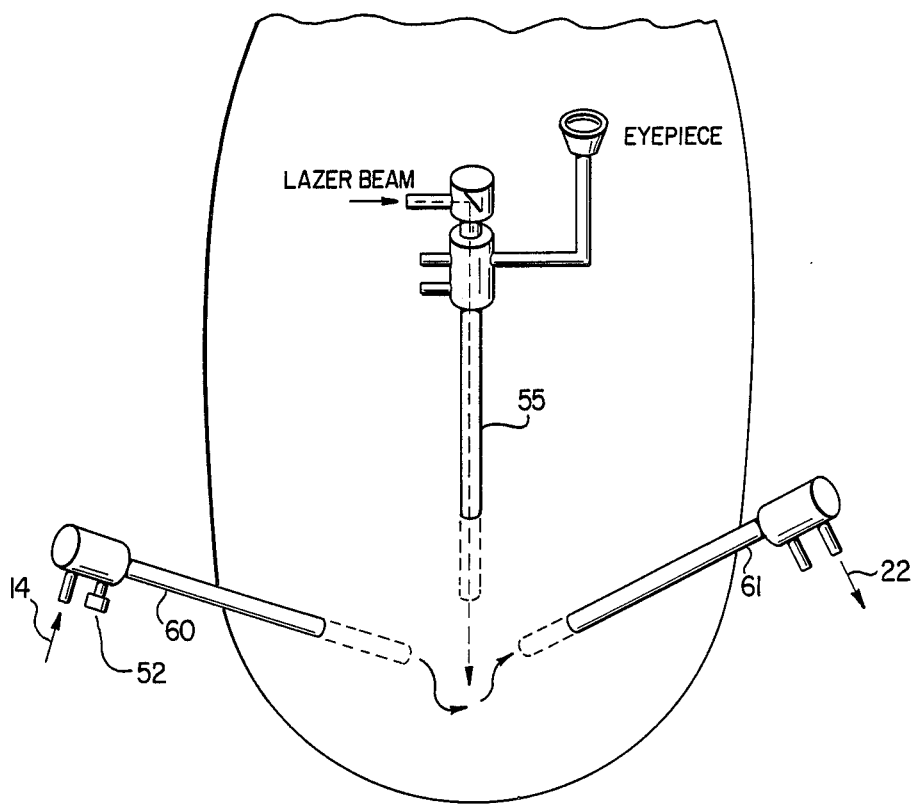
FIG. 6 is fragmentary schematic view in section and elevation showing a triple puncture technique.

Alternatively, as illustrated in FIG. 6, the close circuit system and the insufflator may communicate with the cavity of the patient through a three puncture arrangement in which the laser beam is directed through a laparoscope tube 55 the input $CO_2$ gas and the $CO_2$ gas from the insufflator flows through a second laparoscope 60, and the return of $CO_2$ gas and smoke is through line 22 connected with a third laparoscope 61. Each of the laparoscope tubes 55, 60, and 61 are all standard available laser surgical instruments.

Figure 2:
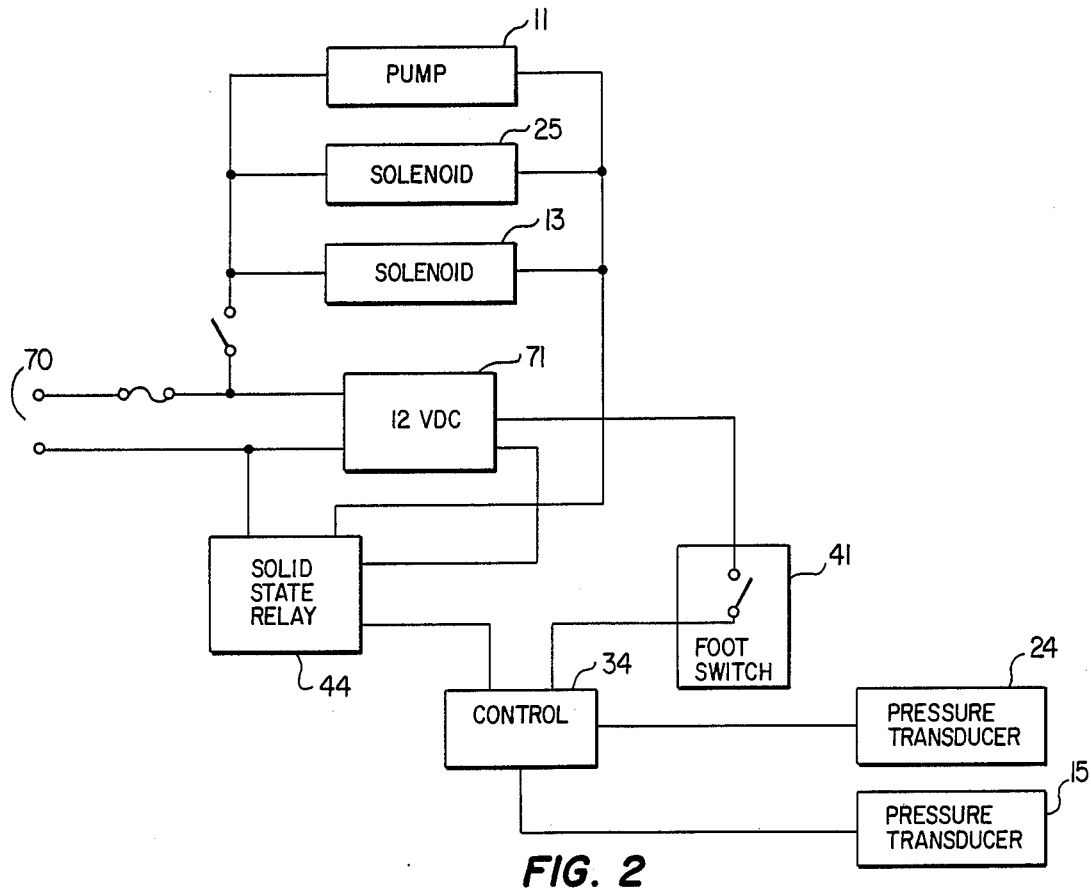
FIG. 2 is a functional schematic diagram of the electrical circuitry employed in the system of FIG. 1.

The electrical supply and control circuitry is shown in FIGS. 2, 3, and 4. Referring to FIG. 2, a suitable source 70 of 115 volt alternating current is connected with a transformer 71 which reduces the electrical power to 12 volts direct current. The transformer is connected through the foot switch 41 and the control circuitry 34 to the solid state relay 44 which is connected with and operates the pump 11 and the solenoid valves 13 and 25. The pressure transducers 15 and 24 are connected with the control circuitry 34. As shown in FIG. 3, the control circuitry 34 includes comparators 70 and 71, a timer 72, and a missing pulse detector 73, which are connected with the pressure transducers 15 and 24 as illustrated. More specific details of the circuitry of the control 34 are shown the wiring diagram of FIG. 4. The pressure transducers 15 and 24 convert $CO_2$ gas pressure in the closed circuit of the system 10 to voltages representing the pressures which are conducted to the comparators 70 and 71. The voltages from the transducers are compared to preset the voltages in the comparitors. If the voltages crosses the preset value set at the comparitors 70 or 71, the output of the comparators changes state. The timer 72 normally produces a pulse train monitored by missing pulse detector 73. When the preset values of a comparator have been crossed, the timer 72 stops producing pulses and the missing pulse detector begins to time out. If no pulses are received by the missing pulse detector within an adjustable time period of approximately one to five seconds, the pump relay and the solenoids are shut down.

Figure 5:
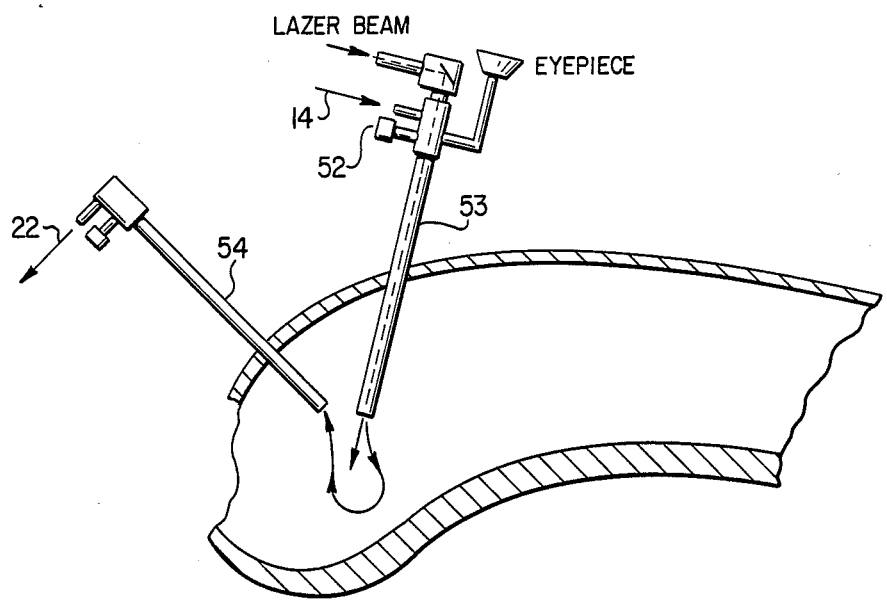
FIG. 5 is a fragmentary schematic view in section and elevation of a patient cavity with the input and discharge laparoscope tubes inserted to the site of the operation using a double puncture technique.

The laparoscopic tubes schematically illustrated in FIGS. 5 and 6 are representative of a variety of different tubular structures which may be used in the system of the invention for accessing the laser beam and the flows of $CO_2$ gas and smoke removal from the site of the operation of the laser. These various laparoscopic tubes are designed to allow visualization of the surgical field within the pelvis, access of the laser beam, and input of $CO_2$ gas to form the closed circuit flow removal of the laser smoke, and $CO_2$ gas and to insufflate and thus distend the abdomen by imposing and maintaining a steady state pressure within the abdomen. The pressure may range from plus 16-20 mm of the gas relative to atmospheric pressure. The insufflation and resulting abdominal distention are necessary to provide adequate increased volume to move pelvic organs about and achieve the necessary visulization and surgical access to the operation site. One form of the laparoscopic tube, such as the tube 53 in FIG. 5, has three channels along its length. One channel carries a fiber optical cable bundle for transmission of illuminating light and the image for visulization of the working field through the eyepiece. A second channel includes a stopcock or valve for controlling the input of insufflating $CO_2$ gas. A third channel is provided for the input of $CO_2$ gas in the closed circuit recirculation system from the pump 11 through line 14. The tube also directs the laser beam to the operating site. Other forms of laparoscopic tubes may contain one or two channels. For example, the tube 61 in FIG. 6 includes two channels, one connected to the line 14 for the input of $CO_2$ gas in the closed circuit system and another channel connected with the line 52 for gas from the insufflator. The other tube 60 shown in FIG. 6 utilizes only a single channel for the return of $CO_2$ gas and laser generated smoke in the recirculation system through the line 22.

The procedure for emplacing laparoscopic tubes includes the following steps. A small incision is made in the skin of the patient, in the navel or just below the navel, and a large needle inserted into the abdominal cavity. The abdominal cavity is then distended with carbon dioxide gas using an abdominal insufflator raising the pressure to the equivalent to 17 to 20 mm of Hg. When the abdomen is properly distended, a trochar is inserted through the same small incision used for the large needle. The trochar is then removed leaving a sleeve for the insertion of a laparoscope. To this point, this is refered to as a "single puncture" technique and typically is used for diagnositic laparoscopy. Where a patient is undergoing laser surgery, usually one or two additional small incisions are made in the lower abdomen above the groin on either side. These incisions then are used for the insertion of the necessary instruments including the laser beam carrying tube, the $CO_2$ gas return flow tube, and insufflator input tube as referred to above in connection with FIGS. 5 and 6.

After the laparoscopic tubes have been inserted in the patient in both the two puncture and three puncture techniques, the required equipment is connected as illustrated in FIG. 1 to provide closed circuit flow of $CO_2$ gas for the evacuation of laser generated smoke, for the makeup supply of $CO_2$ gas, and to maintain abdominal distention from the insufflator. The pump 11 is controlled by the pump impeller speed to provide a maximum flow rate of 1800 in$^3$/min. The gas flow from the pump 11 flows through the line 12, the valve 13, the line 14, the pressure sensor 15, the bacteria filter 20, and into the patient through the laparoscopic tube 53 in the two puncture technique of FIG. 5 or the laparoscopic tube 60 in the three puncture technique shown in FIG. 6. The return flow of the $CO_2$ gas from the patient with the laser generated smoke passes out of the patient through the laparoscopic tube 54 in the two puncture technique, or the laparoscopic tube 61 in the three puncture technique into the line 22, through the smoke filter 23, the pressure sensor 24, through the valve 25, the line 30, the fluid trap 31, and into the suction or return side of the pump 11 to be recirculated to the patient, the smoke and vapor having been removed from the closed circuit flow of the $CO_2$ gas. During this closed circuit flow, flow line pressure values at the pressure sensor 15 and the pressure sensor 24 are maintained at +25 mm Hg and +10 mm Hg, respectively, relative to the atmospheric pressure. During this closed circuit circulation of the $CO_2$ gas, $CO_2$ gas is also injected from the insufflator through the line 52 into the patient through the laparoscopic tube 53 in the two puncture technique or the laparoscopic tube 60 in the three puncture technique. The average abdominal pressure maintained by the insufflator is 16-20 mm Hg. Slow leakage around the laparoscopic tubes and tissue absorption requires only a very small steady state input of $CO_2$ by the insufflator. The control system is set so that if the pressure at the sensor 15 exceeds +25 mm Hg or the vacuum at the sensor 24 falls below 10 mm Hg, the central control module 34 activates the solid state relay 44 effecting the closing of the solenoid valves 13 and 25 isolating the patient from the pump 11. Additional patient safety features include the bacteria and smoke filters 20 and 23 and the fluid trap 31. The smoke filter which typically has a 3 micron pore size removes laser created smoke particles. The bacteria filter filter 20 is designed to capture any filterable microrganisms greater than 0.2 microns in size. The fluid trap 31 removes condensed water vapor which is produced by tissue lasing. Control of safety and over-ride of the operator controlled on-off functions is controlled by the module 34 which is connected in the system as shown in FIG. 4 and schemetically represented in FIG. 3. The electrical output signals from the pressure transducers 15 and 24 are fed into the control module 34. The signals are compared electrically to preset values. If a variation occurs for times exceeding those of typical minor system induced pneumatic transients, typically $\leq$5 seconds, an electrical ouput signal from the control module 34 shuts off the solid state relay 44 which interrupts the 110 volt power supply to the solenoid valves 13 and 25, and to the pump 11, effecting closure of the valves and stopping the pump. The patient is, thus, isolated. Further, the operator has manual control of the on-off state of the system by means of the pedal foot switch 41. The electrical signal from the foot switch 41 enters the system through the control module 34 which will prevent the system from being turned on if a pressure malfunction produces adverses pressure or vacuum circumstances. The system of the invention effectively removes smoke from a pelvis cavity at a rate of up to 1800 cu.in$^3$/min. while maintaining essentially constant volume and average background pressure in the pelvis.

Each of the valves 13 and 25 are three-way diverting valves operated by 110 volt current. The solid state relay 44 is controlled by a 12 volt activation current for switching the 110 volts supply to the pump 11 and to the solenoid valves 13 and 25. The pump 11 is typically of noncorrosive plastic polymer vane and chamber construction. The pressure sensors 24 and 15 are linear voltage differential transformer type with a moveable piston sensing Pg$\leq$76° mm Hg and Pg$\geq$ -76° mm Hg. The foot switch 41 uses a 12 VDC source voltage. Both of the filters use an inert plastic polymeric medium. The power sources typically 115 VAC, 60 HZ, 1.8 AMPS.

When the valve 13 is closed, flow along the discharge side of the pump in the line 12 to the valve 13 is shut off and the valve shunts the pressure in the vacuum side of the patient connecting the lines 14 and 32 thereby equalizing the pressure across the patient. Simultaneously, when the valve 25 closes, the flow along the line 22 into the valve 25 is shut off and the pressure lines 30 and 33 are communicated shunting the in and out ports of the pump isolating the patient from the pump.

It will now be seen that a new and improved apparatus and method for laser smoke evacuation from an operating site in an abdominal cavity has been described and illustrated. The apparatus includes a closed circuit circulation system for $CO_2$ gas wherein $CO_2$ gas is circulate past the operating site, laser smoke produced during the operation is filtered from the $CO_2$ gas and the $CO_2$ gas is recirculated past the operating site. Additionally, $CO_2$ gas is introduced from an insufflator in a separate system for replacing recirculating $CO_2$ gas lost through leakage and tissue absorption, and to maintain the necessary cavity distention for visualization of the operating site and to maintain adequate space for the operation. The procedure and apparatus eliminates the need for large replacement volumes of $CO_2$ gas. Normal problems in maintaining equilibrium physiological blood $CO_2$ gas balance are avoided. The system is useful with any standard laser laparoscopic system.

What is claimed is:

1. A laser smoke evacuation system for removal of $CO_2$ laser produced smoke from a patient cavity comprising:
   means including a tube insertable into said patient cavity for introducing a first flow of $CO_2$ gas into said patient cavity;
   means including a tube insertable into said patient cavity for removal of said first flow of $CO_2$ gas from said patient cavity with any laser smoke mixed therewith;
   means for separating said laser smoke from said first flow of $CO_2$ gas;
   means for returning said first flow of $CO_2$ gas cleansed of said laser smoke to said patient cavity through said tube for introducing said first flow; and means including a tube insertable into said patient cavity for introducing a second makeup flow of $CO_2$ gas into said patient cavity to replace any of said first flow of $CO_2$ gas lost by leakage and tissue absorption and to distend said cavity sufficiently for visualization and access to the working site in said cavity.

2. A laser smoke evacuation system in accordance with claim 1 including control means for maintaining said first and second flows of $CO_2$ gas within predetermined ranges of volumes and pressure.

3. A laser smoke evacuation system in accordance with claim 2 wherein said control means includes means for shutting said system down responsive to predetermined deviations in said pressure and flow ranges.

4. A laser smoke evacuation system in accordance with claim 3 including means for monitoring the pressure of said first flow of $CO_2$ gas entering said patient and means from monitoring the pressure of said first flow of $CO_2$ gas flowing from said patient cavity.

5. A laser smoke evacuation system in accordance with claim 4 including means for balancing the pressure across said patient cavity when said system is shutdown.

6. A laser smoke evacuation system in accordance with claim 5 including means for manually shutting down said system.

7. A laser smoke evacuation system in accordance with claim 5 including filter means for removing bacteria from said first flow of $CO_2$ gas prior to flow into said patient cavity.

8. A laser smoke evacuation system in accordance with claim 7 including fluid trap means for removing fluid from said first flow of $CO_2$ gas prior to flow back into said first flow introducing means.

9. A laser smoke evacuation system in accordance with claim 8 including a shunt flow line for equalizing the pressure across said patient cavity when said system is shutdown.

10. A laser smoke evacuation system in accordance with claim 9 including a shunt flow line for equalizing the pressure across said means for introducing said first flow of $CO_2$ gas.

11. A laser smoke evacuation system for removal of $CO_2$ laser produced smoke from a laser operation site in a patient cavity comprising:
a closed circuit $CO_2$ gas recirculation system including pump means, a discharge line from said pump means, a tube connected with said discharge line and insertable into said patient cavity, a control valve, a pressure sensor, and a bacterial filter in said discharge line between said pump means and said patient, a return line to said pump means, a tube connected with said return line and insertable into said patient cavity, a smoke filter, a pressure sensor, a control valve, and a fluid trap in said return line;
system control means connected with said closed circuit for operating said valves and said pump means responsive to predetermined operating conditions in said closed circuit; and
an insufflator connected with a $CO_2$ supply line, a tube connected with said insufflator and insertable into said patient cavity for supplying makeup $CO_2$ gas to replace $CO_2$ gas lost from said closed circuit system and absorbed by patient tissue and to provide a predetermined pressure for distention of said patient cavity for providing visualization and operating space at said operation site in said cavity.

12. A laser smoke evacuation system in accordance with claim 11 where said tube connected with said discharge line is a first laparoscope tube for positioning through a first puncture into said patient cavity connected with said $CO_2$ gas pump discharge line and with said insufflator and with a laser beam, said first laparoscope tube having means for visually observing the site of impact of said laser beam in said cavity and said tube connected with said return line is a second laparoscope tube for positioning through a second puncture into said patient cavity and connected with said return line to said pump for removing $CO_2$ gas in said closed system and laser smoke from an operation site in said cavity.

13. A laser smoke evacuation system in accordance with claim 11 including a first laparoscope tube for positioning through a first puncture into said patient cavity for conducting a laser beam to an operation site in said cavity, said first laparoscope tube including means for visualization of an operating site in said cavity, said tube to said discharge line is a second laparoscope tube for positioning through a second puncture into said patient cavity and connected with said $CO_2$ gas discharge line from said pump and to a line to said insufflator, and said tube to said return line is a third laparoscope tube for positioning through a third puncture into said patient cavity and connected with said $CO_2$ gas return line to said pump.

14. A laser smoke evacuation system for removal of laser smoke from an operation site in a patient cavity comprising:
a closed circuit $CO_2$ gas system for recirculating $CO_2$ gas through said patient cavity to remove laser smoke from said operation site including a $CO_2$ gas pump, a discharge line from said pump to a first laparoscope tube for positioning into said patient cavity, a first solenoid valve in said discharge line, a pressure sensor in said discharge line downstream from said first solenoid valve, a bacteria removing filter in said discharge line downstream from said pressure sensor, and a first laparoscope tube for connection into said patient cavity for discharging $CO_2$ gas into the operation site at the inward end of said laparoscope tube, a second laparoscope tube for connection into said patient cavity spaced from said first laparoscope tube, a $CO_2$ gas return line from said second laparoscope tube to said pump for recirculating $CO_2$ gas and laser smoke from said operation site, a laser smoke removal filter in said return line downstream from said second laparoscope tube, a pressure sensor in said return line downstream from said smoke filter, a second solenoid valve in said return line downstream from said pressure sensor, a fluid trap in said return line downstream from said second solenoid valve, a first shunt line from said first solenoid valve across to said return line between said pressure sensor in said line and said second solenoid valve, a second shunt line from said second solenoid valve across to said $CO_2$ gas discharge line from said pump connected into said line between said pump and said first solenoid valve, a control module electrically connected with said pressure sensors, a relay connected with said control module and with said first and second solenoid valves for operating said valves responsive to predetermined pressure conditions sensed by said pressure sensors, and a manual switch connected with said control module for manually shutting down the said system; and an insufflator for a connection into said patient cavity through one of said laparoscope tubes for supplying makeup $CO_2$ gas to replace gas lost through leakage and tissue absorption and to maintain a predetermined pressure in said patient cavity to provide operating room at said operation site and permit visualization of said operation site.

15. A laser smoke evacuation system in accordance with claim 14 including a third laparoscope tube for positioning through a third puncture in said patient cavity for said laser beam to said operating site.

16. A laser smoke evacuation method for removing laser smoke from an operation site in a patient cavity during laser laparoscopy comprising the steps of:
   recirculating $CO_2$ gas in a closed system through said patient cavity across said operation site through a supply line tube into said patient cavity and a return line tube into said patient cavity;
   removing laser smoke from said $CO_2$ gas after said gas is discharged from said patient cavity before recirculation of said gas back to said cavity; and
   supplying makeup gas thorugh a tube into said patient cavity independently of said recirculation system for replacing recirculating $CO_2$ gas lost through leakage and tissue absorption and for maintaining a predetermined pressure in said patient cavity for distention of said cavity to permit adequate space at the operation site and provide for visualization of said site.

17. A method in accordance with claim 16 including the step of filtering bacteria from said recirculating $CO_2$ gas prior to input of said gas into said cavity.

18. A method in accordance with claim 17 including monitoring the pressure in said recirculating $CO_2$ gas prior to input into said patient cavity, monitoring the pressure in said recirculating $CO_2$ gas after discharge from said patient cavity, and maintaining the differential between said input and said discharge pressures withing the range of about $+25$ mm Hg above atmospheric pressure on said input side and $+10$ mm Hg relative to atmospheric on said discharge side.

19. A method in accordance with claim 18 wherein the pressure in said patient cavity is maintained within the range of 16–20 mm Hg by said insufflator.

20. A method in accordance with claim 19 including the steps of shutting down said recirculating system when said pressure range between said input and said discharge sides exceed said predetermined value and equalizing the pressure in said patient cavity between said input and said discharge sides.

* * * * *